United States Patent [19]

Lauer et al.

[11] Patent Number: 5,207,886

[45] Date of Patent: May 4, 1993

[54] CAPILLARY ELECTROPHORESIS

[75] Inventors: Henk H. Lauer, Belmont; Paul D. Grossman, Redwood City; Dennis E. Mead, Campbell, all of Calif.

[73] Assignee: Applied Biosystems, Inc., Foster City, Calif.

[21] Appl. No.: 767,345

[22] Filed: Sep. 27, 1991

Related U.S. Application Data

[63] Continuation of Ser. No. 463,796, Jan. 5, 1990, abandoned, which is a continuation of Ser. No. 156,430, Feb. 16, 1988, abandoned.

[51] Int. Cl.$^5$ .................. G01N 27/26; G01N 27/447; B01D 57/02
[52] U.S. Cl. .............................. 204/299 R; 204/180.1
[58] Field of Search ......................... 204/180.1, 299 R

[56]         References Cited

U.S. PATENT DOCUMENTS

| | | | |
|---|---|---|---|
| 3,948,753 | 4/1976 | Arlinger | 204/183.3 |
| 4,898,658 | 2/1990 | Kerger et al. | 204/299 R |

FOREIGN PATENT DOCUMENTS 59-182355  10/1984  Japan ............................. 204/299 R

OTHER PUBLICATIONS

"High-Resolution Separations Based on Electrophoresis and Electroosmosis", Jorgenson, J. W., Lukacs, K. D., *J. of Chromatography*, 218 (1981) pp. 209-216.

"Capillary Zone Electrophoresis", Jorgenson, J. W., Lukacs, K. D., *Science*, vol. 222, 21 Oct. 1983.

"Characterization of a Microinjector for Capillary Zone Electrophoresis", Wallingford, R. A., Ewing, A. G., *Anal. Chem.*, 1987, 59, 681-684.

"Separation of Organic and Metal Ions by High-Voltage Capillary Electrophoresis", Tsuda, T., Nomura, K., Nakagawa, G., *J. of Chromatography*, 264 (1983) pp. 385-392.

"Evaluation of an Automatic Siphonic Sampler for Capillary Zone Electrophoresis", Honda, S., Iwase, S. Fujiwara, S., *J. of Chromatography*, 404 (1987) pp. 313-320.

"Electric Sample Splitter for Capillary Zone Electrophoresis", Demi, M., Foret, F. Bocek, P., *J. of Chromatography*, 320 (1985) pp. 159-165.

"Theory, Instrumentation, and Applications of Capillary Zone Electrophoresis", Lukacs, K. D., Dissertation to University of North Carolina at Chapel Hill, 1983.

"Automatic Liquid Chromatograph Injection and Sampling", Kretz, Wolfgang, and Hans-Georg Hartl, *Hewlett Packard Journal*, pp. 21-24, Apr. 1984.

*Primary Examiner*—John Niebling
*Assistant Examiner*—John S. Starsiak, Jr.
*Attorney, Agent, or Firm*—Joseph H. Smith; Donald R. Boys; Ronald E. Grubman

[57]         ABSTRACT

An apparatus is disclosed for providing capillary electrophoresis, which includes an electronically controlled valve system for automatically introducing a sample into the capillary by means of a vacuum at the end of the capillary tube. This approach of sucking in the sample is extremely accurate and reproducible, and results in a minimum of band broadening. Furthermore, it enables the entire capillary electrophoresis system to be easily automated. An automated temperature control system is provided which enables the temperature of the capillary tube (and hence the solvent/solute system) to be controlled during electrophoresis, thereby very directly controlling pH and electrophoretic mobility. In another embodiment, the capillary is prewashed and equilibrated to achieve substantially zero charge on the capillary wall, thereby essentially eliminating electroosmotic flow and substantially improving resolution.

3 Claims, 3 Drawing Sheets

| Run Number | Buffer | pH Level | Elution time Electroosmotic Flow (min) | Pre-Wash | Electroosmotic Mobility $10^{-4}$ cm$^2$/Vs |
|---|---|---|---|---|---|
| #1 | Caps (10 mM) | pH = 11.13<br>pH = 11.13 | t = 1.70<br>t = 1.63 | NaOH<br>HCl | 8.2<br>8.5 |
| #2 | Bicene (10 mM) | pH = 8.45<br>pH = 8.45 | t = 1.64<br>t = 1.93 | NaOH<br>HCl | 8.5<br>7.2 |
| #3 | MES (10 mM) | pH = 6.0<br>pH = 6.0 | t = 2.09<br>t = 6.27 | NaOH<br>HCl | 6.7<br>2.2 |
| #4 | MES (10 mM) | pH = 6.0<br>pH = 6.0 | t = 2.07<br>t = 4.80 | NaOH<br>HCl | 6.7<br>2.9 |
| #5 | Citric Acid (20 mM) | pH = 4.0<br>pH = 4.0 | t = 11.82<br>t = 54.6 | NaOH<br>HCl | 1.2<br>0.25 |
| #6 | Citric Acid (20 mM) | pH = 2.51<br>pH = 2.51 | t = 36.53<br>t = 70.31 | NaOH<br>HCl | 0.38<br>0.2 |

Fig. 2

CAPILLARY ELECTROPHORESIS

CROSS-REFERENCE TO RELATED APPLICATION

This is a continuation of application Ser. No. 463,796, filed Jan. 5, 1990, now abandoned, which was a continuation of application Ser. No. 156,430, filed Feb. 16, 1988, now abandoned.

BACKGROUND OF THE INVENTION

This invention relates to capillary electrophoresis, or as it is more conventionally called "capillary zone electrophoresis" (CZE), and more particularly to automated methods and apparatus for introducing samples into capillary columns and for improving separations by using temperature control of said columns.

In recent years significant advances have been made in micro-column separation techniques. A principal advantage of such techniques is their suitability for analysis of extremely small sample volumes, e.g. in the microliter or submicroliter amounts of sample. Being able to analyze such small volumes has become exceedingly important with the explosion of research in the biological field, because often-times biological samples are quite small.

One of the significant problems with capillary techniques is in introducing sample into the capillary. One technique used in capillary electrophoresis, called sample injection, is electromigration, a term collectively including the effects of eletrophoresis and electro-osmosis (See Jorgenson, J. W. and Lukacs, K. D., *J. Chromatography*, 1981, Vol. 218, pp. 209-216; Jorgenson, J. W., and Lukacs, K. D., *Science*, 1983, Vol. 222, pp. 266-272; and Wallingford, R. A. and Ewing, A. G., *Anal. Chem.*, 1987, Vol. 59, pp. 681-684). In this technique, one end of the capillary and the electrophoresis anode are placed into the sample and a voltage is briefly applied, causing a small band of sample to electromigrate into the capillary. This method of sample injection suffers from discrimination within the sample because solutes with higher mobilities will preferentially migrate into the electrophoresis column and therefore change the relative composition of the sample. To avoid this problem, attempts to physically inject sample have also been reported (Jorgenson and Lukacs, *Science*, ibid). However these direct injection techniques cause band broadening, apparently due to the laminar flow profile introduced during the injection.

Other less common injection methods include gravity flow (See Tsuda, A., et al, *J. Chromatography*, 1983, Vol. 264, pp. 385-392.), siphoning (See Honda, S. et al, *J. Chromatography*, 1987, Vol. 404, pp. 313-320.), and the use of an electonic sample splitter (See Deml, M. et al, *J. Chromatography*, 1985, Vol. 320, pp. 159-165.). Each of these injection techniques are capable of placing subnanoliter volumes of sample into the electrophoresis column with a minimum of band broadening. However, the gravity flow or siphoning injection method is inaccurate and lacks precision in providing absolute volume amounts due to the unreliable position of the sample level which will change due to the sample withdrawal. The latter can only be neglected if the original sample volume is large compared to the volume injected. With the electronic splitter, a larger initial sample volume is required in order be able to split it down to the smaller size required for the column. Thus, some sample may be wasted, or there may not be sufficient sample to perform a separation. Also, this latter technique is further complicated by requiring an additional controlled power supply or very careful control of the electric resistances in the different legs of the splitter. Furthermore, the need to use an initial larger sample size significantly decreases the number of applications for which it can be used.

What is needed is a simple, automatable, sample injection technique that is suitable for microvolumes, is capable of providing accurate sample volumes, and which produces a minimum of band broadening.

SUMMARY OF THE INVENTION

In accordance with preferred embodiments of the invention, an apparatus is disclosed for providing capillary electrophoresis, which includes an electronically controlled valve system for automatically introducing a sample into the capillary by means of a vacuum at the end of the capillary tube. This approach of sucking in the sample is extremely accurate and reproducible, and results in a minimum of band broadening. Furthermore, it enables the entire capillary electrophoresis sytem to be easily automated.

The apparatus includes first and second reservoirs that are electrically isolated from each other for holding electrophoretic media, a sample reservoir located in proximity of the first reservoir for holding a sample to be electrophoresed, and a high voltage power supply connected between the first reservoir and the second reservoir. A first pressure source of a first gas having a first known pressure, typically the ambient air pressure, is used for providing an environment for the first reservoir and the sample reservoir, so that electrophoretic media in the first reservoir and sample in the sample reservoir are under the first pressure. The apparatus includes a pressure reservoir for holding a second gas (also typically air) having a second pressure that is lower than the first pressure. A capillary tube is also included in which to electrophorese the sample. A rack system is provided for holding the first and second reservoirs, the pressure reservoir, the high voltage power supply, the sample reservoir, and for holding one end of the capillary tube in the second reservoir. A gas connecting system connects the second reservoir to the pressure reservoir, the connecting system having a valve for venting the connecting system to the first pressure source and for blocking communication of the second reservoir with the pressure reservoir while venting to the first pressure source. The apparatus also has an insertion element for inserting the other end of the capillary tube into the sample reservoir and into the first reservoir. In the preferred mode, the apparatus includes a computer system for controlling the insertion element and the valve, so that when the other end of the capillary tube is in the sample reservoir, the valve permits communication of the second reservoir with the pressure reservoir for a controlled period of time for sucking the sample into the capillary tube. Additionally, in the preferred mode, the computer system causes the other end of the capillary tube to be transferred to the first reservoir after the sucking of the sample into the capillary tube. After the sample has been introduced into the capillary tube and the tube has been transferred to the first reservoir, the electrophoresis is begun.

An additional important feature of the preferred embodiment is that an automated temperature control system is provided which enables the temperature of the capillary tube (and hence the solvent/solute system) to be controlled during electrophoresis. This is particularly advantageous in that for many buffers, the pH is a strong function of temperature; hence temperature control is very directly pH control. Additionally the pH can have a direct effect on the electrophoretic mobility and hence the separation efficiency.

In another embodiment of the invention, the capillary is prewashed and equilibrated to achieve substantially zero charge on the capillary wall, thereby essentially eliminating electroosmotic flow and substantially improving resolution.

BRIEF DESCRIPTION OF THE DRAWINGS

FIG. 2 is a table that illustrates the effects of capillary prewash on electroosmotic mobility.

DESCRIPTION OF THE PREFERRED EMBODIMENTS

Figure 1:
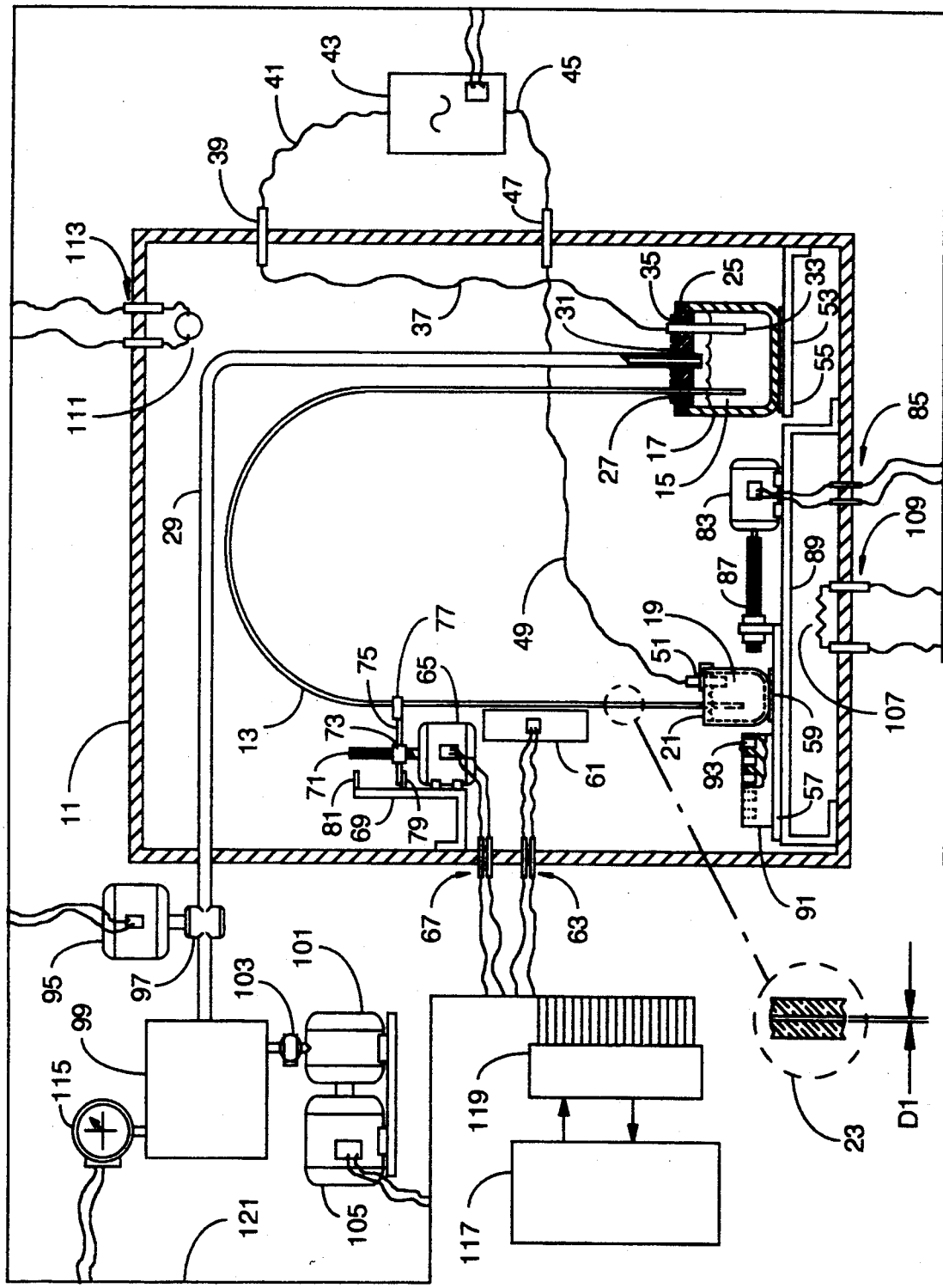
FIG. 1 shows an apparatus according to the invention.

FIG. 1 is a partially sectioned illustration of a preferred embodiment of an automated capillary electrophoresis, henceforth CZE, apparatus according to the invention. In this preferred mode, the apparatus includes an environmental enclosure 11, which has access openings (not shown), and feedthroughs of various kinds through the walls of the enclosure for elements that must be connected to elements outside the enclosure. Electrophoresis is accomplished within the enclosure in a capillary tube 13, preferrably constructed of fused silica, such as is typically used for high sensitivity liquid or gas chromatography. One end of capillary 13 is immersed for the process in a buffer solution 19 held in a first container 21, and the other end is immersed in a buffer solution 15 in a second container 17. Buffer solutions 15 and 19 are typically the same solution, and many are well known in the art. Although in the prior art many different pH's have been used for the various buffers, depending on the particular experiment being performed, in this preferred embodiment, it has been found that for capillary electrophoresis that a relatively low pH is best. In the preferred mode, to achieve the best separations, the pH is adjusted to the point of zero electric charge of the buffer-capillary combination, i.e. the point at which there is no charge on the capillary wall. As will be discussed subsequently in more detail, the point of zero charge will vary depending on the buffer used and the pretreatment of the column. However, as a practical matter, typically a pH below about 2.5 will suffice. Also, as will be discussed subsequently, sometimes particular buffers are used which are temperature dependent, i.e. their pH varies strongly with temperature, or stated another way dpK/dT is relatively large.

View 23 is an enlargement of capillary tube 13 in cross section. The internal diameter of the capillary, D1, varies for different kinds of samples and for other reasons. A typical value for D1 is 0.05 mm, and generally varies between zero and 200 microns. The wall thickness of tube 13 is small enough that the tube is flexible and may generally be manipulated without breaking. Also, the small diameter allows for effecient heat transfer.

Second container 17 has an airtight top 25. Capillary tube 13 enters the second container through a stopper 27 maintaining an airtight seal. There are two additional penetrations through top 25. A hollow tubing 29 enters through stopper 31 and an electrode 33 enters through another stopper 35. Stopper 35 is typically of an electrically non-conducting material. From electrode 33, an electrical lead 37 goes to an electrical feedthrough 39 which allows an electrical signal or power to cross the wall of the enclosure without shorting to the enclosure. On the outside, electrical lead 41 goes to a terminal of a high voltage power supply 43.

From the opposite terminal of power supply 43 another electrical lead 45 goes to another feedthrough 47. Inside the enclosure lead 49 goes to an electrode 51 immersed in buffer solution 19 in first container 21. With buffer solution and sample material in the capillary tube and the tube ends immersed in buffer solution in the two containers, power supply 43, through the electrical leads, feedthroughs and electrodes, may be used to maintain an electrical potential across the material in the capillary tube.

The second container rests on a support 53 with an electrical insulator 55 between the container and the support. The insulator is needed if the container and support are electrically conductive. First container 21 rests on a moveable, sliding support 57 and an insulator 59.

A detector 61 is positioned relative to the capillary tube to measure the results of electrophoresis in the capillary. Such detectors are well known in the art, and include for example an Applied Biosystems Model 783 Spectroflow UV/Visible Detector, which is a variable wavelength programmable detector that is specifically adapted for on-column detection. Electrical leads through feedthroughs 63 carry power and signals for the instrument. There may be more than the two leads shown.

When the electrophoresis process is complete on one sample, and another sample is wanted in the capillary for analysis, a new sample may be loaded without manual intervention or disturbing the environmental enclosure. A motor 65 powered by leads through feedthrough 67 and supported by bracket member 69 may be activated to turn lead screw 71. Nut 73 is attached to member 75 with a clamp 77 securely holding tube 13, so that turning lead screw 71 will raise and lower the tube by the distance between stops 79 and 81. This distance is set to be sufficient for the lower end of capillary tube 13 to be raised above the rim of container 21, and lowered again.

With tube 13 raised above the rim of container 21, motor 83 may be activated by leads through feedthroughs 85 to turn lead screw 87 moving slide 57 along support 89. A sample container 91 with multiple microvolumes such as 93, arranged in a row in the container, is prepared in advance and placed adjacent to container 21 on slide 57. Each microvolume may contain a sample to be analyzed. Typical injection volumes range from 1 nl to 10 nl in this preferred mode, although other size samples could of course be chosen depending on the size of the reservoir used to hold the sample and the size of the column. By controlling motor 83 moving slide 57, any one of the microvolumes of container 91 may be moved to be directly below the end of capillary tube 13, which may then be lowered into the microvolume by control of motor 65. Once a new sample is drawn into the capillary, the capillary may again be raised, container 21 returned to position, and the end of the capillary re-immersed in the buffer by lowering the tube.

To inject a new sample, while one end of the capillary is in one of the microvolumes of sample material, a relative vacuum is drawn in second container 17 by means of tubing 29 which exists the environmental enclosure. Motor 95 is controlled to rotate a three-way rotary valve 97 opening tubing 29 to vacuum reservoir 99. The reservoir is maintained at desired vacuum level by vacuum pump 101 through isolation valve 103. A vacuum sensing gauge 115 with programmable signal points monitors the vacuum level in reservoir 99. The pump is powered by motor 105. Careful control of timing and vacuum level provides a very accurate method for drawing a predetermined amount of sample material into the capillary, as well as other benefits. As an example, using a pressure differential of 5.0 in. of Hg between the vacuum reservoir and the enclosure 11, with a 65 cm long fused silica capillary having a 50 micron inside diameter, a 2 second open time for valve 97 results in an injection quantity of 5 nanoliters of an aqueous solution.

Another important feature of the apparatus according to the invention is that the temperature inside the environmental enclosure 11 can be controlled. A heating element 107 is powered through feedthroughs 109 to provide heat, and a heat sensing element 111 monitors temperature through leads 113. As will be discussed subsequently, such provision for temperature control is very useful, since some buffers have a temperature dependent pH, and for those buffers pH can be controlled automatically by controlling temperature. Temperature control is also useful in the more general case since other kinds of variations are avoided if a uniform temperatur is used throughout a separation. For example, viscosity and therefore mobility are most often strong functions of temperature, so that for reproducability, temperature control is required.

Power and control leads for all the electrical equipment associated with the apparatus of the preferred embodiment are carried by electrical conduit 121 to a control interface 119 which provides power terminations and switching of signals for control purposes. The control interface is connected to and manipulated by a computer 117 which can be pre-programmed so that critical parameters may be maintained and sequences of analyses may be performed automatically by the apparatus. For example, the vacuum level desired can be entered as control data, and the computer, through the control interface, monitors the signal from vacuum gauge 115 and opens and closes vacuum isolation valve 103 so that the desired vacuum level is closely maintained. As another example, the computer can be used to control the temperature inside the environmental enclosure by monitoring temperature sensor 111 and controlling power to heating element 107 as needed to maintain the programmed temperature. Also, the computer can be programmed to allow a sequence of analyses to be made, using the several samples preloaded into microvolumes in container 91, controlling the electrical devices in the required sequence. The program may be set to run analyses on all of the microvolume samples, one-after-the other, or to allow for manual intervention and initiation between each analysis. Another important feature of computer control is that the computer makes it possible to reverse polarity of the capillary electronically. Hence, for solutes that are of opposite charge, one can reverse the direction of migration of solute particles and thereby use the UV detector at its fixed location.

Details of the program structure for the computer are provided in Appendix A.

Control of pH

In capillary electrophoresis in free solution and in some gels, solutes with different charges (absolute) have different electrophoretic mobilities and can therefore be separated. Separation efficiency can be improved if the selectivity (i.e. the relative difference in electrophoretic mobility) between two or more solutes can be changed during the eletrophoretic run. One way to achieve this is to change the relative difference in the effective charges on the species to separated. In many cases the pH (or better, the pK) of the solution in the capillary, which is mostly buffer, determines the charge on solutes that obey the rules of acid/base equilibria. For example, for CHES (Cyclohexyl amino ethane sulfonic acid) in water, a chemical equilibrium is established which is dependent on the particular temperature, as indicated by the following formula:

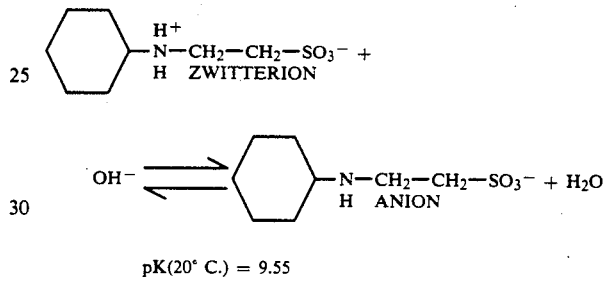

$pK(20° C.) = 9.55$ at pH=9.55, 50% of the CHES is in the zwitterion form and 50% is in the anion form. By increasing the pH to 10.55, the anion ($RSO_3^-$) concentration will be ten times that of the zwitterion and by increasing it to 11.55, the equilibrium will be pushed almost completely to the anion side. At that point only 1% of the CHES will exist as a zwitterion. The anion will posess a certain electrophoretic mobility while the zwitterion being electrically neutral will not have an electrophoretic mobility. What this means is that at a pH of about 7.55, the CHES solute will have practically no electrophoretic mobility and at a pH of about 11.55, it will have nearly the mobility of the anion. Hence, by changing the pH of the solution, the mobility of a solute can be changed.

As indicated earlier, in many cases, the pH (or pK) of buffer solutions are a function of their temperature, and different buffer solutions have different temperature characteristics. (See CALBIOCHEM CATALOG, Table IV, Page 16.) By changing the temperature of the buffer in time or in space, different pH's in time and in space can be generated and thus the mobility of a species can be manipulated. In general, the pK of a solution is given by:

$$pK = pH - \log\{RSO_3^-\}/\{R^+SO_3^-\},$$

where $\{RSO_3^-\}$ corresponds to the concentration of the anion $RSO_3^-$, etc., and in many cases the pK has a strong temperature dependence. As an example of how to use this temperature dependence during the performance of a separation, suppose that a separation is to be performed on a solution containing three solutes, A, B, and C, and that the A and B separation is best performed at a first temperature T1 with A coming through first, and that the B and C separation is best performed at a temperature T2. The separation is run for a first time at temperature T1, until A is separated from B and C, then the temperature is changed to T2 until B and C are separated. Similarly, more complicated temperature profiles can be used depending on the particular solutes being separated, for example continuous programming can be used if desired.

It should be appreciated by those skilled in the art that solutes that are to be separated may also obey the acid/base equilibria rules, and as a result also can change their degree of ionization with temperature. This solute effect will be superimposed on the pH change of the solvent (buffer) and hence, depending on the choice of buffer and solute combination, can provide an enhanced mobility difference, decreased mobility difference, or no change in mobility difference at all. Hence, various combinations of buffer and solute should be chosen to achieve the desired effect.

As a specific example of the effects of varying temperature, and hence pH, an experiment was conducted to investigate the relative electrophoretic mobilities of two proteins, Myoglobin (wsm) and Myoglobin (hh). A fused silica capillary was used having a 55 cm length to the detector, a total length of 70 cm, and an inside diameter of 0.050 mm. Using a 10 mM Tris-HCl buffer, and a 20 kV electric potential, the change in relative difference in electrophoretic mobilities (i.e. selectivity) of the two proteins was measured between the temperatures of 26.9° C. (pH=8.90) and 62.4° C. (pH=7.90), and was found to be minus 45%

As described earlier, another important aspect of the invention in achieving a high selectivity, particularly in protein separations, is to eliminate charge on the capillary wall. The purpose is to eliminate electroosmotic flow, so that the column is not being swept during the run, thereby providing a longer separation time in the column (lower average velocity of the species to be separated), and hence better resolution. Also, by eliminating charge on the wall, positive ions (e.g. proteins) do not stick to the wall, unlike the typical case when the wall is negatively charged. One way to achieve zero charge on the wall is through control of pH. Generally, the electroosmotic velocity is proportional to the zeta potential times the applied electric field divided by the viscosity. The zeta potential describes electrostatic forces in the interfacial double layer between two phases and is, among others, a function of the differential adsorption of ions. When there is no electroosmotic flow, the zeta potential is zero, and there is no charge on the capillary wall. Hence, by measuring the electroosmotic mobility, i.e. the electroosmotic velocity divided by the applied field, as the pH is changed to achieve zero mobility, the point of zero charge on the wall can be determined.

Figure 3:
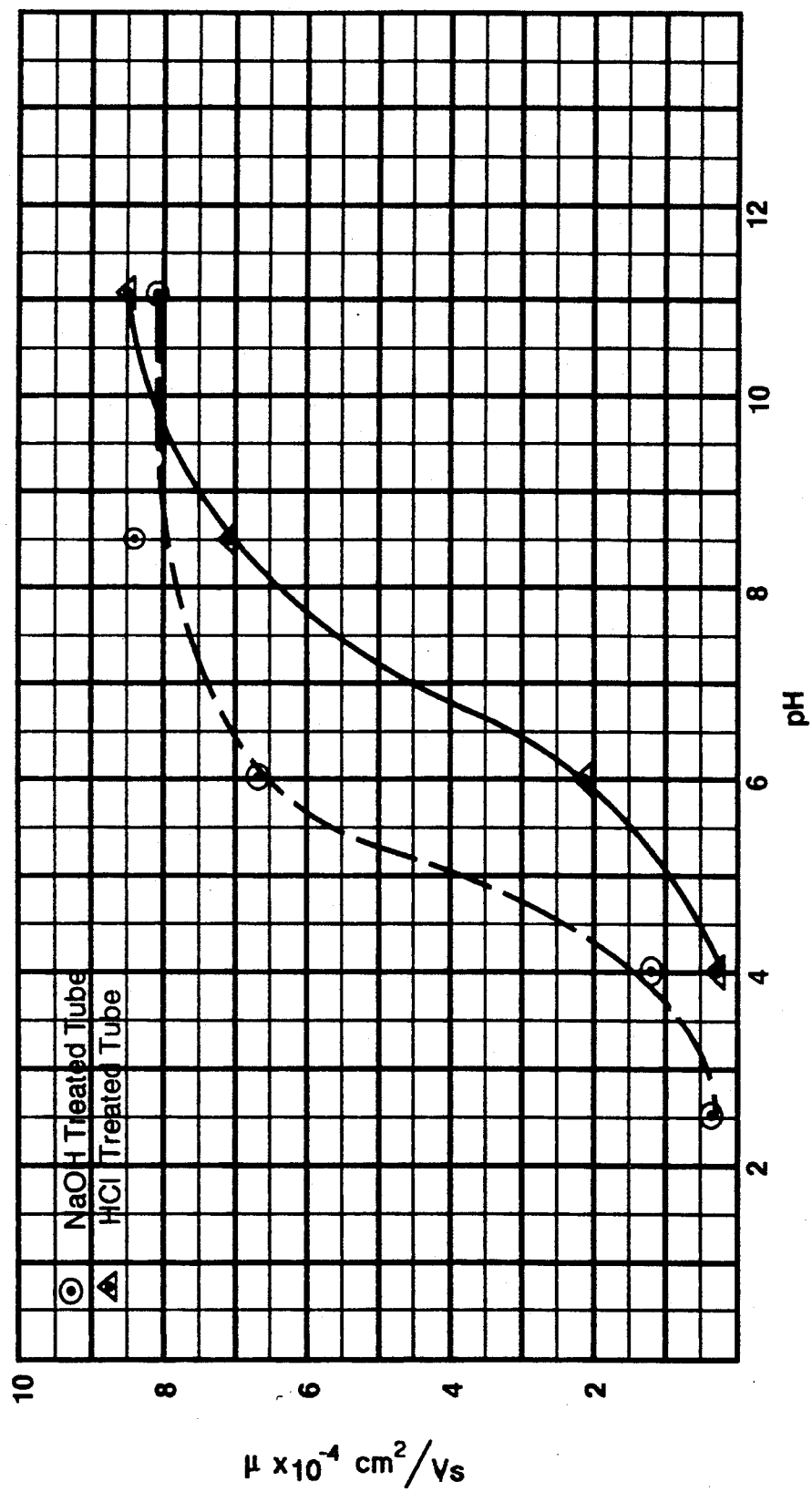
FIG. 3 is a graph showing the results of FIG. 2.

An example of the effects on electroosmotic mobility resulting from pH changes and some surprising results from differences in capillary preparation are illustrated in the Table of FIG. 2, and in FIG. 3. In these experiments, a number of buffers were used in order to cover a wide range of pH levels, since as a general rule any one buffer has a relatively limited range of pH values over which it is useful. The capillary used was a fused silica capillary supplied by Polymicro Technologies, and had a length to the detector of 30 cm, a total length of 50 cm, and an inside diameter of 0.050 mm. The applied electric field used was 360 V/cm. Except for run 4, where the order of preparation was reversed to check for reversibility (i.e. steps 4, 5, and 6, preceeded steps 1, 2, and 3 below), the protocol for capillary preparation was as follows:

1. wash capillary with 1M NaOH for 3 minutes;
2. equilibrate with buffer for 5 minutes;
3. run with mesityl oxide as a neutral marker and measure elution time for the marker;
4. wash capillary with 1M HCl for 3 minutes;
5. equilibrate with buffer for 5 minutes;
6. run with mesityl oxide and measure elution time.

The buffers used were CAPS (i.e. 3-(cyclohexylamino) propane sulfonic acid), BICINE (i.e. N,N-bis(2-hydroxyethyl) glycine), MES (i.e. a sodium salt of 2-(N-morpholino) ethane sulfonic acid), and citric acid.

A graph of the electroosmotic mobility, shown in FIG. 3, illustrates dramatically the results of lowering the pH. Clearly, as the pH is lowered there is a sharp decrease in mobility indicating that the charge on the wall is quickly approaching zero. For NaOH treated tubes, a pH of below about 2.5 corresponds essentially to zero electric charge on the wall (the baseline noise is proportional to the current, so as a practical matter it is important to use a low current, and low pH buffer). Even more striking, however, is the effect of the prewash. Although NaOH is the quintessential strong base that is typically used for washing glass, it is clear that the use of a strong acid such a HCl is a much better prewash if the purpose is to eliminate charge on the capillary wall. For example, if the capillary prewash is performed with HCl, a pH of about 4.0 eliminates about 97% of the charge on the capillary wall, and produces an electroosmotic mobility that is even lower than that achieved using a pH of 2.5 if the prewash is with NaOH. Furthermore, it appears that the effects of the different prewashes are substantially independent of each other, since in run 4 where the order of the two prewashes was reversed, the results are substantially the same. As a practical matter, it appears that removing 95% or more of the charge on the capillary wall is important in performing high resolution capillary electrophoresis, regardless of the prewash that is used. However, it appears that eliminating that charge is much easier to accomplish, and allows use of a much higher and more easily attained pH level, if the capillary is prewashed with an acid instead of a base before the run.

It will also be appreciated by those skilled in the art that there are several ways to control the temperature of the solvent/solute system. For example, one way has already been described which uses a heater system for environmental chamber 11. Another approach would be to use one or more electrical heaters wrapped around the capillary tube, and another would be to use one or more pieces of insulating wrap on the capillary tube. Those skilled in the art will undoubtedly be able to think of other equivalent methods for controlling the temperature to effect electrophoretic mobility. Those skilled in the art will also understand that in some instances it may be preferred to not have all components inside the enclosure 11. For example, the detector sometimes may be located outside the enclosure along with the corresponding portion of the capillary where the UV detection is to take place. Such an approach would facilitate service of the UV detector system. Also, instead of raising and lowering the capillary, one could raise and lower the sliding support to insert and remove the capillary from the sample and buffer reservoir. It should also be apparent that one could use electrophoretic media other than aqueous solutions, for example organic fluids could also be used, a specific example being acetonitrile.

What is claimed is:

1. An apparatus for capillary electrophoresis comprising:
   a capillary tube in which to electrophorese a sample;
   high voltage power supply means for providing an electrical potential difference between opposite ends of said capillary tube;
   injection means for injecting said sample into said capillary tube;
   heating means for heating said capillary tube;
   detection means for detecting said sample in said capillary tube;
   first reservoir means for holding a first volume of an electrophoretic solution;
   second reservoir means for holding a second volume of an electrophoretic solution;
   holding means for holding said capillary tube, said high voltage power supply means, said injection means, said heating means and said detection means, for holding said first reservoir means in proximity of a first end of said capillary tube, and for holding said second reservoir means in proximity of a second end of said capillary tube.

2. Apparatus as in claim 1 wherein said injection means comprises:
   sample reservoir means for holding said sample; and
   translation means for moving said first end of said capillary tube from said sample reservoir means to said first reservoir means.

3. Apparatus as in claim 1 wherein said heater means heats said capillary tube according to a preprogrammed schedule that varies the temperature of the capillary tube during electrophoresis.

* * * * *